US011219751B2

(12) United States Patent
Jagadeesan et al.

(10) Patent No.: US 11,219,751 B2
(45) Date of Patent: Jan. 11, 2022

(54) CATHETER DEVICES, SYSTEMS AND METHODS FOR INJECTION OF ADHESIVE MATERIALS

(71) Applicant: Regents of the University of Minnesota, Minneapolis, MN (US)

(72) Inventors: Bharathi Dasan Jagadeesan, North Oaks, MN (US); Sean Lester Moen, Saint Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 181 days.

(21) Appl. No.: 14/937,058

(22) Filed: Nov. 10, 2015

(65) Prior Publication Data
US 2016/0129220 A1 May 12, 2016

Related U.S. Application Data

(60) Provisional application No. 62/077,426, filed on Nov. 10, 2014.

(51) Int. Cl.
*A61M 39/06* (2006.01)
*A61B 17/00* (2006.01)
(Continued)

(52) U.S. Cl.
CPC ....... *A61M 39/06* (2013.01); *A61B 17/00491* (2013.01); *A61B 17/12109* (2013.01);
(Continued)

(58) Field of Classification Search
CPC .............. A61M 39/06; A61M 25/0097; A61M 2039/062; A61M 2025/0004; A61M 5/19;
(Continued)

(56) References Cited

U.S. PATENT DOCUMENTS 4,323,065 A * 4/1982 Kling .................... A61M 39/12
604/533
4,795,439 A * 1/1989 Guest ................ A61M 25/0009
138/115
(Continued)

FOREIGN PATENT DOCUMENTS

CN 1198683 A 11/1998
WO WO2013177549 11/2013

OTHER PUBLICATIONS

Codman, a Johnson & Johnson Company, *TruFill® n-BCA Liquid Embolic System: Proven and Effective AVM Treatment,* © 2009, 4 pages.
(Continued)

*Primary Examiner* — Brandy S Lee
*Assistant Examiner* — Hong-Van N Trinh
(74) *Attorney, Agent, or Firm* — Patterson Thuente Pedersen, PA (57) ABSTRACT

Embodiments relate to a system for providing a first fluid and a second fluid. The system includes a catheter hub, a flexible cover, and a catheter. The flexible cover is configured to attach to the catheter hub and provide a seal therewith. The catheter is configured to be at least partially arranged within the catheter hub and the flexible cover and pass through the seal. The catheter includes a primary lumen and a secondary lumen, wherein the primary lumen is configured to provide the first fluid at a distal end of the catheter, and the secondary lumen is configured to provide the second fluid at each of a plurality of apertures arranged on an outer radial wall of the catheter.

10 Claims, 9 Drawing Sheets

(51) Int. Cl.
*A61B 17/12* (2006.01)
*A61M 25/00* (2006.01)

(52) U.S. Cl.
CPC .............. *A61B 17/12186* (2013.01); *A61B 2017/0065* (2013.01); *A61B 2017/00495* (2013.01); *A61B 2017/00641* (2013.01); *A61B 2017/00849* (2013.01); *A61M 25/0097* (2013.01); *A61M 2039/062* (2013.01); *A61M 2202/0468* (2013.01)

(58) Field of Classification Search
CPC ...... A61M 2025/0098; A61M 25/0032; A61M 2025/0037; A61M 2025/0057; A61M 25/007; A61B 17/00491; A61B 2017/00495; A61B 2017/0065; A61B 17/12109; A61B 17/12186; A61B 2017/00849
See application file for complete search history.

(56) References Cited

U.S. PATENT DOCUMENTS

| | | | | |
|---|---|---|---|---|
| 4,795,739 | A * | 1/1989 | Lifson | A61K 36/42 424/758 |
| 4,968,307 | A * | 11/1990 | Dake | A61M 25/007 604/264 |
| 5,053,004 | A * | 10/1991 | Markel | A61M 5/1582 29/428 |
| 5,156,596 | A * | 10/1992 | Balbierz | A61M 25/0097 604/164.11 |
| 5,256,144 | A | 10/1993 | Kraus | |
| 5,318,517 | A * | 6/1994 | Reiman | A61M 1/0084 128/207.14 |
| 5,405,334 | A * | 4/1995 | Roth | A61M 25/0014 604/264 |
| 5,817,072 | A * | 10/1998 | Lampropoulos | A61M 25/0017 604/264 |
| 6,053,900 | A * | 4/2000 | Brown | A61M 25/0017 604/500 |
| 6,146,373 | A * | 11/2000 | Cragg | A61B 17/12022 604/19 |
| 6,780,183 | B2 | 8/2004 | Jimenez | |
| 2002/0049423 | A1 * | 4/2002 | Howell | A61B 18/14 604/528 |
| 2003/0144623 | A1 * | 7/2003 | Heath | A61M 25/0023 604/4.01 |
| 2005/0113893 | A1 * | 5/2005 | Saab | A61M 25/0009 607/105 |
| 2007/0239105 | A1 | 10/2007 | Weitzner | |
| 2007/0239151 | A1 | 10/2007 | Atalar | |
| 2013/0023770 | A1 | 1/2013 | Courtney | |
| 2014/0012193 | A1 * | 1/2014 | Qiu | A61M 25/0032 604/96.01 |

OTHER PUBLICATIONS

EV3 Your Endovascular Company, *Onyx Les Liquid Embolic System*, © 2009, 2 pages.
Covidien, Vascular Therapies Product Catalogue, Neurovascular, 2014 edition, 14 pages.
Medtronic, *Covidien Neurovascular Micro Catheter Receives FDA Approval*, Jun. 10, 2014, 2 pages.
Terumo Interventional Systems, *Progreat® Microcatheter Product Overview*, © 2016, 6 pages.
DePuy Snythes, Products, 3 pages, © 2015.
Stryker, Products—Neurovascular Intervention, © 1998-2016, 1 page.
Velat GJ, "Comparison of N-butyl cyanoacrylate and onyx for the embolization of intracranial arteriovenous malformations: analysis of fluoroscopy and procedure times," Neurosurgery. Jul. 2008: 63, 8 pages.

* cited by examiner

CATHETER DEVICES, SYSTEMS AND METHODS FOR INJECTION OF ADHESIVE MATERIALS

RELATED APPLICATION

The present application claims the benefit of U.S. Provisional Application No. 62/077,426 filed Nov. 10, 2014, which is hereby incorporated herein in its entirety by reference.

TECHNICAL FIELD

Embodiments relate generally to catheters and more particularly to catheters and related systems and methods for injection of adhesive material, such as glue, during intracranial embolization and other procedures.

BACKGROUND

TRUFILL glue (n-butyl Cyanoacrylate) is a liquid embolic material that is used to treat intracranial vascular disorders such as dural arteriovenous fistulas (DAVF) and arteriovenous malformations (AVM). It is also finding increasing use in the treatment of peripheral vascular malformations and embolization of acutely bleeding vessels. TRUFILL glue has an extremely fast set up time, very similar to that of super glue; in fact, TRUFILL and super glue have almost identical chemical signatures. Because of this many physicians are hesitant to use TRUFILL glue due to apprehension that the glue delivery catheter may get stuck in the vessel during the embolization process. The embolization also has to occur very rapidly before the glue solidifies around the tip of the delivery catheter and adheres the catheter tip to the vessel wall. If the catheter does adhere to the vessel wall or other tissue, it can lead to adverse consequences such as stroke, arterial rupture and severe bleeding. That being said, TRUFILL glue is a very time-efficient way to treat abnormal vasculature.

One known method for mitigating the potential of the catheter becoming stuck during embolization is to provide dextrose to inhibit premature polymerization of the TRUFILL glue. In some known embolization processes, a physician directs the catheter to the desired position, and performs angiography. Once the physician is sure the catheter is in the correct position, TRUFILL is mixed with ethiodol to a specified concentration, typically between 2 and 3 parts ethediol to 1 part glue. The physician primes the catheter lumen and hub dead space with 5% dextrose. Dextrose prevents the activation of n-butyl cyanoacrylate by inhibiting the binding of glue to free ions prior to its interaction with blood. Then the glue mixture is injected through the catheter. Once the delivery of the glue mixture is complete, the catheter is removed quickly to avoid sticking (for example, a 150 cm catheter can be "pulled" in less than 1 second). Often it only takes one catheter to complete a glue embolization, but in the occasion that another injection is necessary, a new catheter is required.

Another liquid embolic material used for intracranial embolization is ONYX, a compound consisting of dimethyl sulfoxide, ethylene vinyl alcohol and tantalum. While ONYX has the benefit of a longer working time, it also is associated with the downside of the patient receiving larger doses of radiation, and the case time is greatly lengthened. The recommended ONYX injection rate is 0.1 ml per minute, or 10 minutes per ml. Furthermore, head-to-head studies of ONYX with glue have failed to demonstrate any differences in the rate of catheter retention. For example, a study in the journal of Neurosurgery (Yelat G J, "Comparison of N-butyl cyanoacrylate and onyx for the embolization of intracranial arteriovenous malformations: analysis of fluoroscopy and procedure times," Neurosurgery. July 2008: 63) discusses benefits of TRUFILL over ONYX in this regard (TABLE 1).

TABLE 1

Showing fluoroscopy and procedure times in a series of patients who underwent endovascular embolization of brain arteriovenous malformations using glue or Onyx.

|  | Glue Injection | Onyx Injection | Reduction with Glue |
| --- | --- | --- | --- |
| Mean fluoroscopy and procedure time | 37 min | 57 min | 20 min |
| Cumulative mean and fluoroscopy time | 64 min | 135 min | 71 min |
| Cumulative mean procedure time | 222 min | 320 min | 102 min |

Therefore, while each embolic material has its place, and one cannot take the place of the other in every case, in most situations requiring embolization it is acceptable to use either material. In these instances, glue is often the preferred embolic material as it saves a great deal of radiation dose to the patient and can be done with a much shorter case time while producing the same results.

To address the specific issue of catheter retention from the catheter becoming adhered, a specific catheter was developed for ONYX injection. The catheter, called APOLLO, could potentially be used for glue as well. The APOLLO catheter has a distal tip that can be separated in the event that the catheter becomes stuck in the embolic material. It comes in two separation lengths, 15 mm and 30 mm, and reduces the amount of foreign body left in a patient in the unfortunate event that the catheter becomes embedded in embolic material. But the APOLLO catheter does not prevent or solve the problem of embedment in embolization; rather, it reduces the negative effects of such an event. The APOLLO catheter is also stiff to navigate and difficult to track within very small vessels. Further, the catheter tip does not always detach.

In summary, while some physicians therefore prefer glue, others with less experience may be hesitant to use glue due to the fear of the catheter adhering. Developing a better delivery system for glue that reduces the likelihood that the catheter will adhere therefore could result in increasing confidence in the use of glue and wider adaptation by more physicians in embolization procedures. This in turn can significantly decrease radiation dose to patients, especially children, decrease procedure times and improve efficacy of treatment.

SUMMARY

Embodiments relate to systems for providing a first fluid and a second fluid. In an embodiment, the system comprises a catheter hub, a flexible cover, and a catheter. The flexible cover is configured to attach to the catheter hub and provide a seal therewith. The catheter is configured to pass through the catheter hub and the flexible cover. The catheter comprises a primary lumen and a secondary lumen. The primary lumen is configured to provide the first fluid at a distal end, and the secondary lumen is configured to provide the second fluid at each of a plurality of apertures arranged on an outer radial wall of the catheter.

The above summary is not intended to describe each illustrated embodiment or every implementation of the present invention. The figures and the detailed description that follow more particularly exemplify these embodiments.

BRIEF DESCRIPTION OF THE DRAWINGS

Embodiments may be more completely understood in consideration of the following detailed description in connection with the accompanying drawings, in which.

While embodiments are amenable to various modifications and alternative forms, specifics thereof have been shown by way of example in the drawings and will be described in detail. It should be understood, however, that the intention is not to limit to be limited to or by the particular embodiments depicted and described. On the contrary, the intention is to cover all modifications, equivalents, and alternatives falling within the spirit and scope of the appended claims.

DETAILED DESCRIPTION

Embodiments relate to catheters and related systems and methods for injection of adhesive material, such as glue, during intracranial embolization and other procedures. In embodiments, a catheter comprises a primary lumen for delivery of glue or another material and a secondary lumen for infusion of an anti-binding or other material, such as dextrose in one embodiment, to the distal tip area of the catheter and/or its outer radial wall. In one embodiment, the primary lumen is a central lumen, and the secondary lumen is a peripheral lumen, extending around 360 degrees of the outer circumference of the primary lumen in a serpentine or helical manner along at least a portion of the length of a distal portion of the catheter. The secondary lumen can comprise at least one radially external aperture to infuse a material therein along an external surface of the distal portion, thereby preventing the glue or other material in the primary lumen from causing the distal portion of the catheter to adhere to a vessel wall or other tissue.

As used herein unless otherwise noted, "distal" generally refers to the delivery or insertion end or portion of the catheter, remote from the physician or medical professional controlling the catheter, while "proximal" generally refers to the opposite end, the one closer to the physician or medical professional.

Figure 1A:
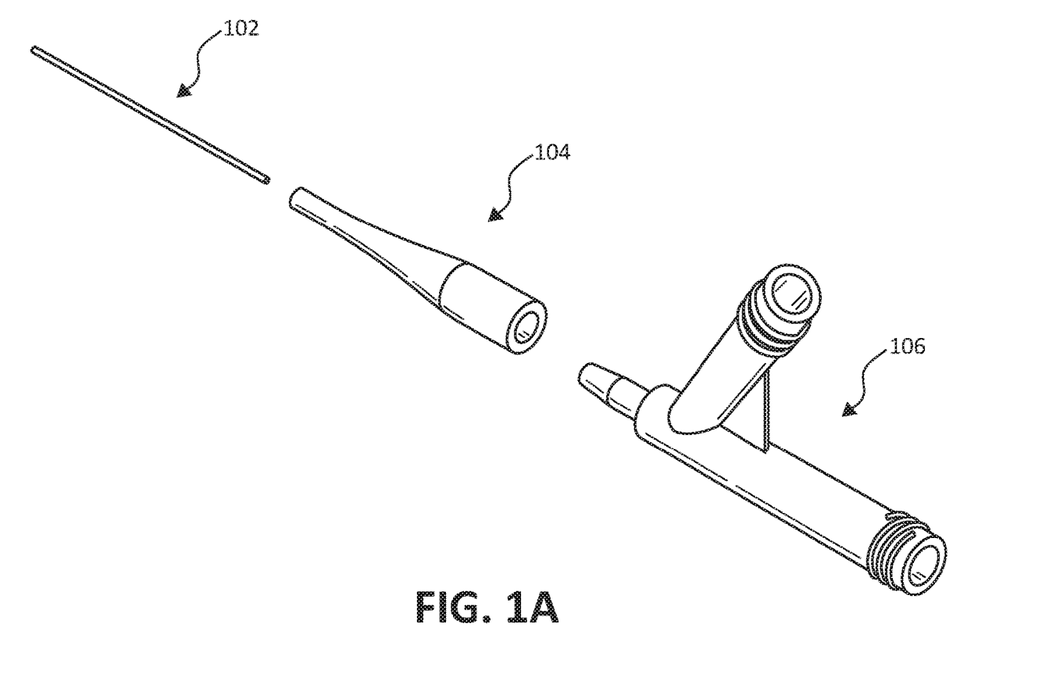
FIG. 1A is an exploded view of a system for embolization, according to an embodiment.
Figure 1B:
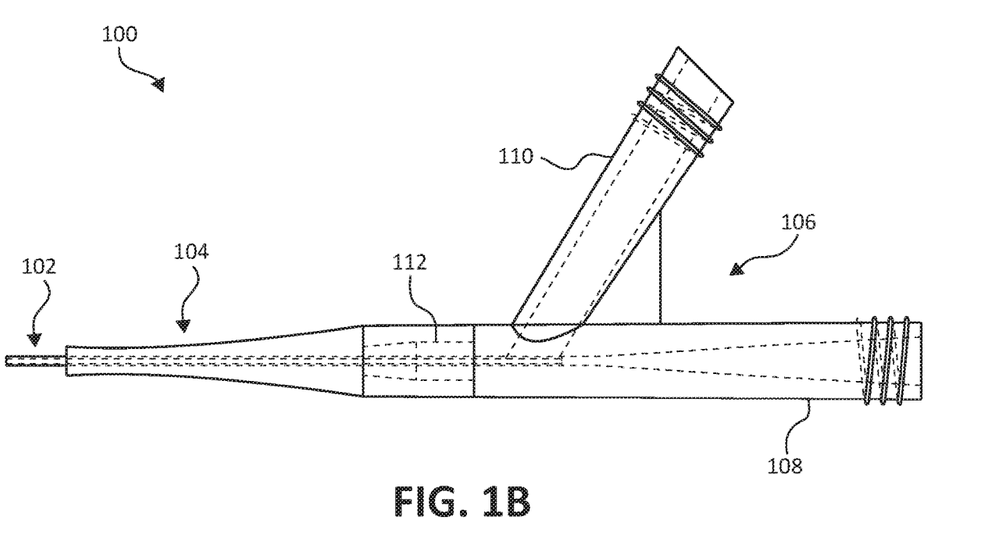
FIG. 1B is a plan view of the system of FIG. 1A, with internal components shown in phantom.

Referring to FIGS. 1A and 1B, system 100 is depicted. System 100 includes catheter 102, flexible cover 104, and catheter hub 106. System 100 is capable of providing an embolizing agent via catheter 102. For example, system 100 can be used to deliver a dose of TRUFILL adhesive to a DAVF or AVM. System 100 not only permits delivery of the embolizing agent but also protects against sticking between the embolization site and catheter 102.

Catheter 102 is a device that can be routed through a vein, artery, or other area to the desired site of embolization to provide the embolizing agent. As such, catheter 102 can be a tube or cable, having a primary lumen (114, see FIG. 2A) defined by a radially interior wall of catheter 102 and configured to carry the embolizing agent (e.g., TRUFILL, ONYX, other embolizing agents, or any other fluid). In addition, catheter 102 can discharge a second substance along its exterior radial wall via a helical secondary lumen (116, see FIG. 2A). For example, catheter 102 can discharge a dextrose solution along the exterior wall to prevent sticking of catheter 102 to an embolization site.

Flexible cover 104 is configured to engage with catheter 102 to prevent blood from flowing upstream (i.e., from the distal end of catheter 102 towards catheter hub 106). Flexible cover 104 provides a substantially fluid-tight seal with catheter 102. Flexible cover 104 is also configured to engage in a fluid-tight manner with catheter hub 106. In some embodiments, flexible cover 104 is made of a flexible plastic.

In the embodiment shown, catheter hub 106 is a hub having a Y-shape. The Y-shape of catheter hub 106 is formed by three legs: first leg 108, second leg 110, and third leg 112. First leg 108 and third leg 112 are substantially collinear with one another as shown in FIGS. 1A and 1B, but in other embodiments the legs can be at a variety of relative angles with respect to one another.

In embodiments, various types of catheter hubs can be used to provide primary fluid flow through to primary lumen and secondary fluid flow to a secondary lumen without intermixing. As such, catheter hubs can be any devices capable of providing a region for the introduction of the second substance to the secondary lumen 116 of catheter 102, as described previously. In embodiments, the catheter hub comprises a valve. In some such embodiments, catheter hub 106 comprises a hemostatic valve. In alternative embodiments, even in the absence of a valve, the catheter hub can provide a substantially hemostatic connection point for the catheter, a source of the first fluid, and a source of the second fluid, due to the relative sizes and/or shapes of the various components that interact at the hub. For example, the fit between the catheter hub and the catheter can be substantially hemostatic.

FIG. 1B shows system 100 of FIG. 1A in an unexploded view. In the view shown in FIG. 1B, catheter 102 passes from the distal end (shown on the left in this view) through flexible cover 104, and into third leg 112 of catheter hub 106. Catheter 102 terminates, on its proximal end, within the body of catheter hub 106. On the distal end, catheter 102 is routed to the desired site of embolization (not shown).

Figure 2A:
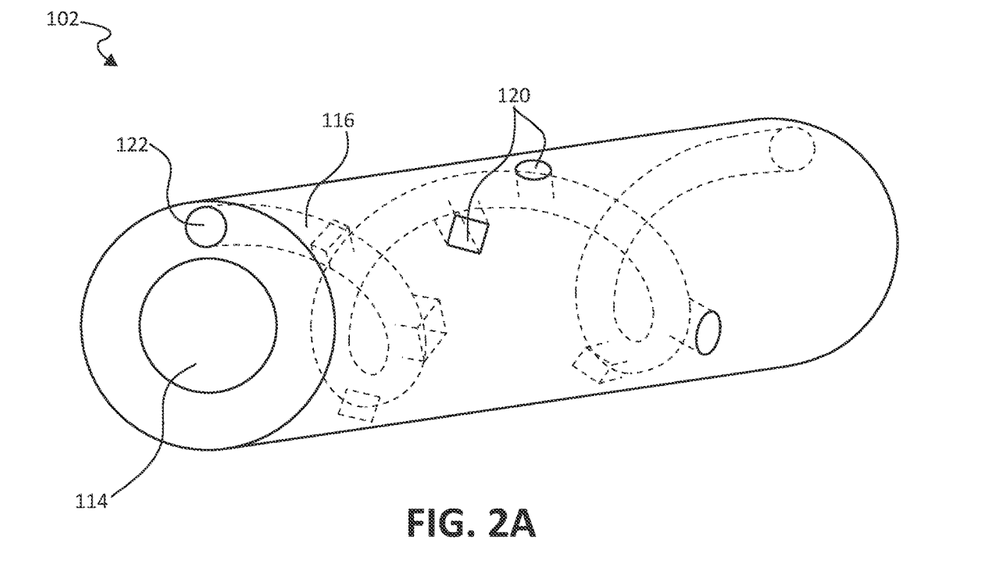
FIG. 2A is a partial perspective view of a catheter according to an embodiment.

According to FIG. 2A, a distal portion of catheter 102 is depicted in a perspective view. As previously described, catheter 102 comprises a primary lumen 114 and a helical, secondary lumen 116. Primary lumen 114 can be a central lumen (i.e., with a center of a circumference of primary lumen 114 aligned with a center of an outer circumference of catheter 102), with the outer circumference of catheter 102 being larger than the circumference of primary lumen 114. In other embodiments, primary lumen 114 can be non-central with respect to catheter 102.

Secondary lumen 116 is arranged within catheter 102 around primary lumen 114 in a serpentine or helical manner along at least a distal portion of catheter 102, and comprises a plurality of apertures 120 spaced apart along at least a portion of its length adjacent to the distal end, as well as an end aperture 122. Apertures 120 can be evenly spaced in some embodiments, or the spacing of apertures 120 can vary in other embodiments. For example, apertures 120 closest to the distal tip of catheter 102 (i.e., the surface that defines the end aperture 122) can be more closely spaced with respect to one another, while apertures 120 further away from the distal tip can be less closely spaced with respect to one another. Apertures 120 can be round, square, oblong or any other shape, with the shape either being the same or varying amongst apertures 120. In general, however, the spacing, configuration and number of apertures 120 is such that a fluid in secondary lumen 116 can be distributed from secondary lumen 116 to sufficiently bathe the exterior of catheter 102 and prevent the primary material delivered by primary lumen 114 from causing catheter 102 to adhere to a vessel wall or other tissue. In one example embodiment, each aperture 120 is generally round with a diameter of about 0.003 inches to about 0.005 inches, and adjacent apertures 120 are spaced apart from one another by about 0.1 inches to about 0.5 inches.

In the embodiment shown in FIG. 2A, end aperture 122 is an aperture positioned in the far distal end of catheter 102. As such, end aperture 122 routes a fluid within secondary lumen 116 in a primarily longitudinal direction with respect to catheter 102, substantially parallel to the direction of glue or other embolic material dispensed from primary lumen 114. As such, end aperture 122 can inhibit premature polymerization along and around the distal tip of catheter 102, while the other apertures 120 can inhibit premature polymerization along outer radial wall 118 of catheter 102.

In other embodiments, secondary lumen 116 can be replaced by some other secondary lumen having, for example, a different pitch to the helix defined by the secondary lumen, or in other embodiments the secondary lumen could be non-helical. Such alternative secondary lumens could be arranged in any fashion that would provide a secondary fluid at a sufficient portion of outer radial wall 118 to inhibit premature polymerization and prevent sticking of catheter 102 to the embolization site. Likewise, various alternative embodiments can have multiple secondary lumens or split secondary lumens to provide different output patterns for the secondary fluid (e.g., dextrose solution) dispensed.

Primary lumen 114 and secondary lumen 116 are isolated from one another within catheter 102 such that a material in primary lumen 114 cannot flow to secondary lumen 116 along the length of catheter 102, and vice-versa, except as any materials may commingle proximate the distal tip of catheter 102 after being delivered or infused from the respective lumens 114 and 116 in normal and intended use. This ensures that the integrity of both materials, particularly that of the glue, other embolic agent or other material in primary lumen 114, is not compromised during delivery.

Figure 2B:
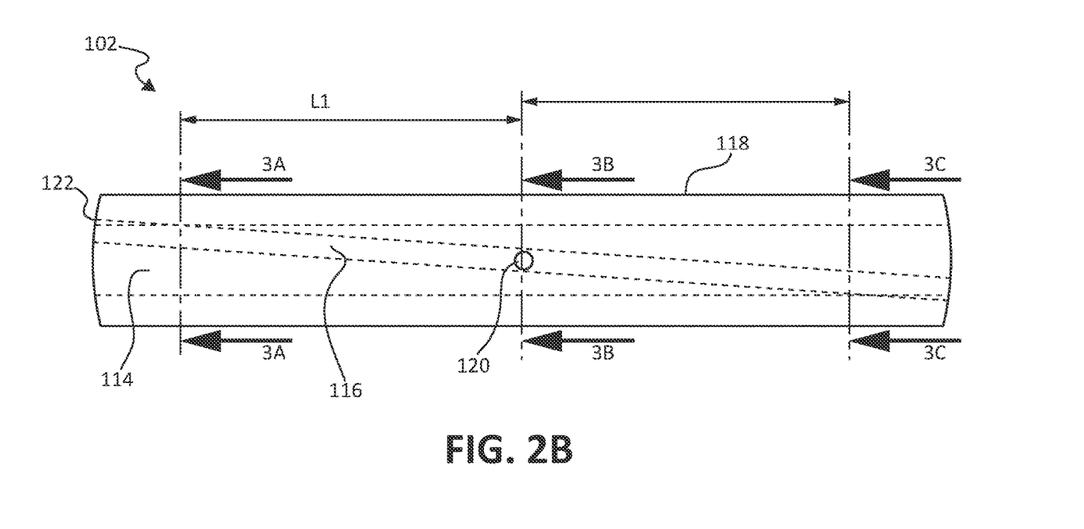
FIG. 2B is a plan view of the catheter of FIG. 2A, with internal components shown in phantom.

FIG. 2B shows catheter 102 in plan view, with primary lumen 114 and secondary lumen 116 shown in phantom. In the section shown in FIG. 2B, secondary lumen 116 makes about one-quarter orbit around primary lumen 114. Cross-sections 3A-3A, 3B-3B, and 3C-3C are defined. The cross-sections are spaced apart from one another by distances L1 and L2 as shown. Cross-section 3B-3B bisects an aperture 120.

Figure 3A:
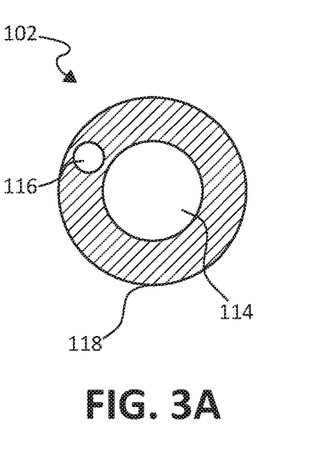
FIGS. 3A-3C are cross-sectional views of the catheter of FIGS. 2A and 2B across lines 3A-3A, 3B-3B, and 3C-3C, respectively.
Figure 3B:
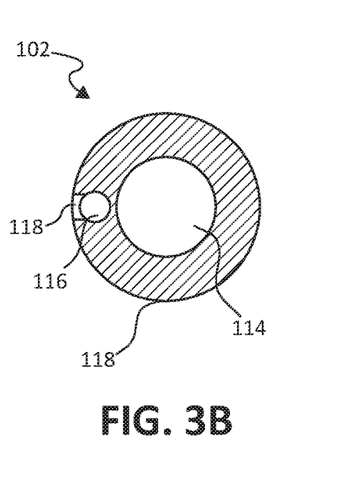
Figure 3C:
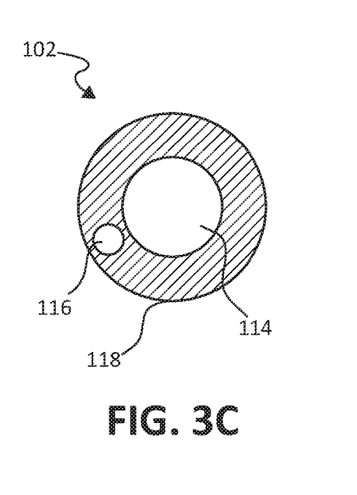

FIGS. 3A-3C are cross-sectional views of catheter 102 taken from cross-sections 3A-3A, 3B-3B, and 3C-3C as shown in FIG. 2B. FIGS. 3A-3C depict the orbit of secondary lumen 116 about primary lumen 114. In the embodiment shown, length L1 (FIG. 2B) is approximately 0.077 inches, whereas Length L2 (FIG. 2B) is approximately 0.074 inches, in the embodiment shown. Over the course of that total distance, 0.150 inches, secondary lumen 116 makes approximately one quarter rotation about primary lumen 114. These exact dimensions are merely exemplary of one possible embodiment, and in other embodiments they can vary based upon the desired use, the age and size of the intended person or animal in which catheter 102 is to be used, etc., as will be appreciated by those of skill in the art. In alternative embodiments, the period of rotation as a function of distance along catheter 102 can vary. FIG. 3B shows a cross-section of an aperture 120, which permits flow of a fluid contained by secondary lumen 116 to outer radial wall 118 of catheter 102.

Figure 4A:
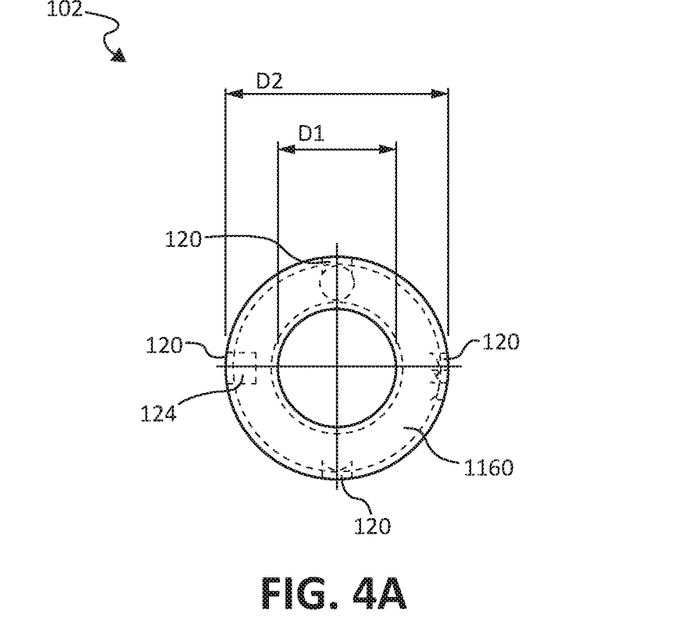
FIGS. 4A and 4B are end views of the catheter of FIGS. 2A and 2B.
Figure 4B:
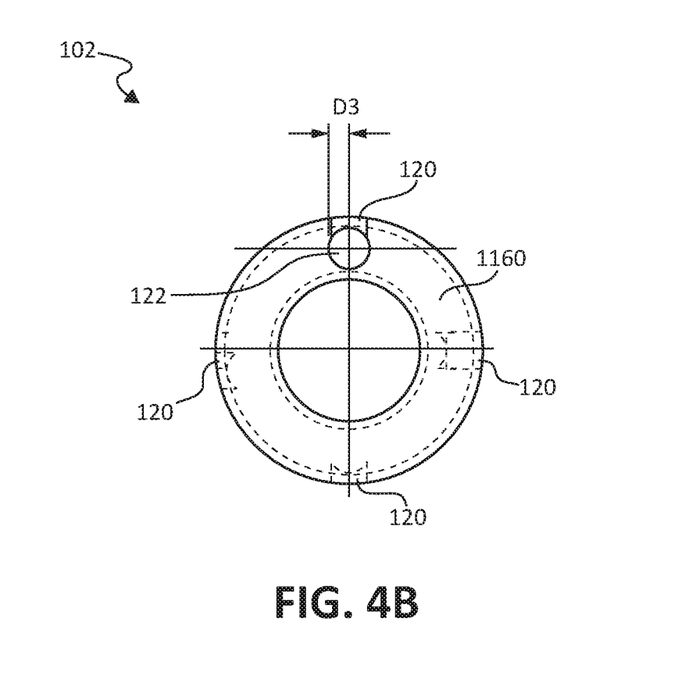

FIGS. 4A and 4B are end views of catheter 102. In particular, FIG. 4A depicts an end view of catheter 102 from the proximal end, whereas FIG. 4B depicts an end view of catheter 102 from the distal end. Elements that are not visible from the end are nonetheless shown in phantom.

FIG. 4A shows catheter 102 having an inner diameter D1 and an outer diameter D2. Within inner diameter D1 is a centrally-located lumen, primary lumen 114. Catheter 102 is substantially solid between inner diameter D1 and outer diameter D2, except for a helically rotating lumen, secondary lumen 116 (for simplicity, secondary lumen 116 is shown in the end view of FIGS. 4A and 4B as helical lumen orbit 1160). Secondary lumen 116 is in fluid communication with a plurality of apertures 120 that extend from helical lumen orbit 1160 radially outwards to the outer limit of diameter D2, such that outer radial wall 118 is also in fluid communication with the secondary lumen 116. FIG. 4A depicts trench 124, through which fluid can be routed into secondary lumen 116 at the proximal end.

As shown in FIG. 4B, end aperture 122 has a diameter D3. In the embodiment shown in FIG. 4B, diameter D3 is about 0.005 inches. In alternative embodiments, diameter D3 can be various sizes to generate a desired flow rate at the distal end, or to create a desired pressure profile throughout secondary lumen 116, for example.

Figure 5A:
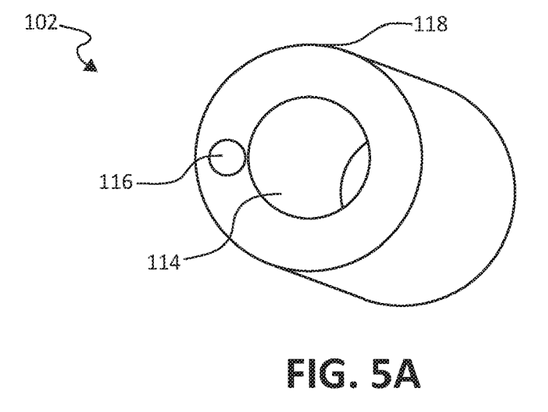
FIGS. 5A-5C are perspective views of the catheter of FIGS. 2A and 2B taken at cross-sections along the length of the catheter.
Figure 5B:
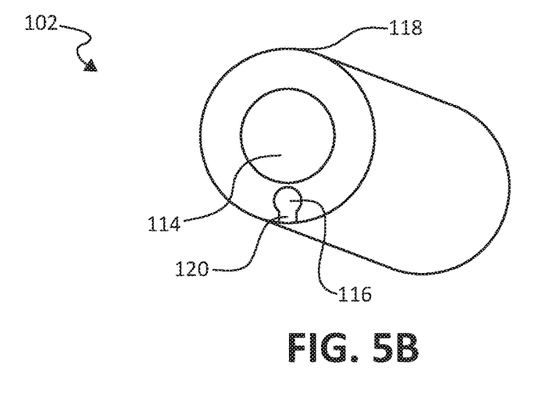
Figure 5C:
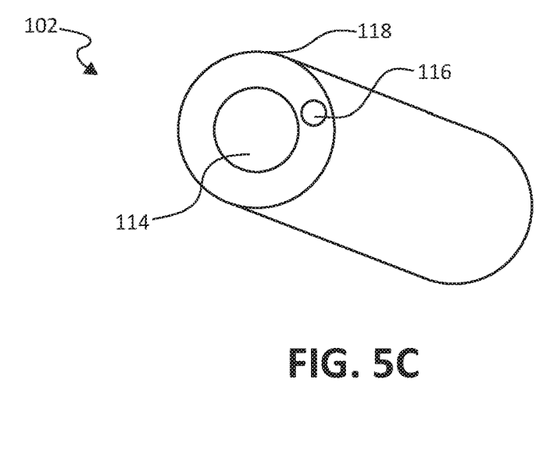

FIGS. 5A-5C are perspective views of catheter 102 taken at various cross-sections perpendicular to its length. Similar to FIGS. 3A-3C, these cross-sections show the orbit of secondary lumen 116 about primary lumen 114. FIG. 5B shows an aperture 120 in outer radial wall 118 of catheter 102 that facilitates fluid communication from secondary lumen 116 to outer radial wall 118.

Figure 6A:
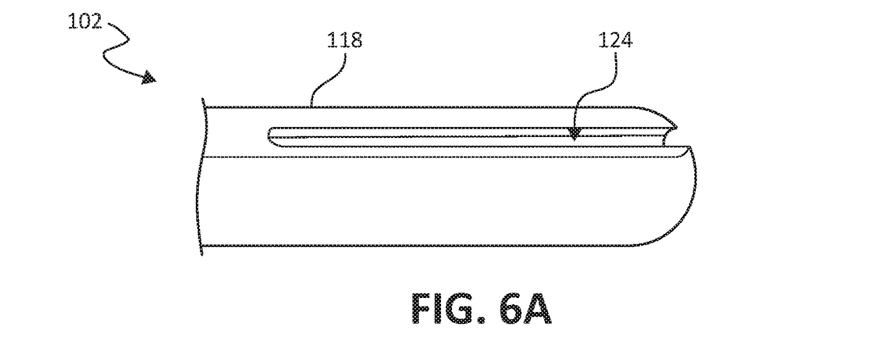
FIGS. 6A and 6B are perspective views of the catheter of FIG. 2A at its proximal end.
Figure 6B:
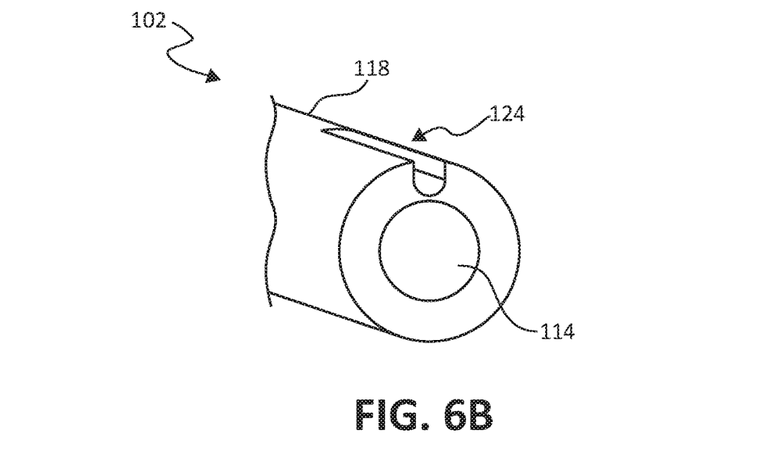
Figure 6C:
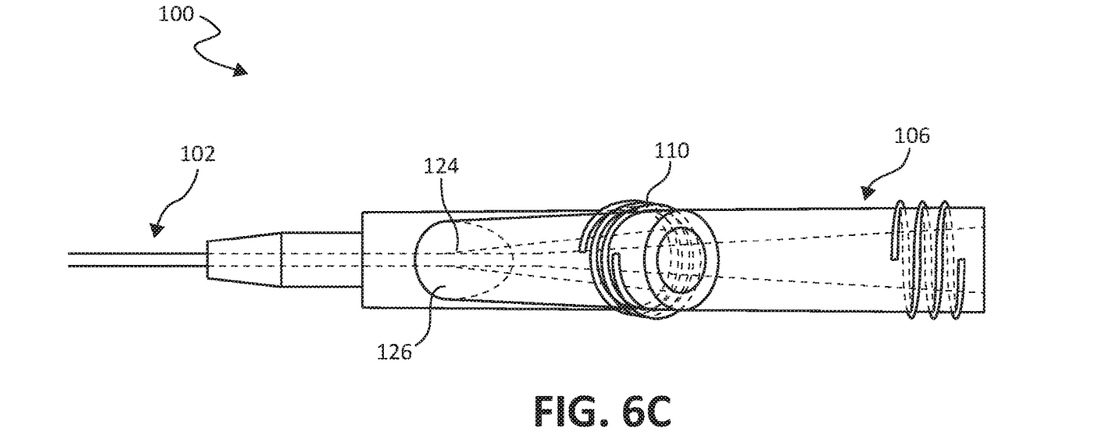
FIG. 6C is a top view of the system of FIGS. 1A-1B, with internal components shown in phantom.

FIGS. 6A-6B show the proximal end of catheter 102, depicting trench 124. FIG. 6C is a plan view of catheter 102 positioned within catheter hub 106 such that second leg 110 creates a secondary fluid inlet region 126 that is adjacent to the trench 124.

Trench 124 is an extended aperture along outer radial wall 118. Trench 124 is in fluid communication with secondary lumen 116, such that as fluid at positive pressure is brought into contact with trench 124, that fluid will be routed through the secondary lumen 116 towards the distal end and out of the various apertures 120, 122, as previously described. As shown in FIGS. 6A-6C, trench 124 is substantially parallel to catheter 102, unlike the remainder of secondary lumen 116, which follows a curved path. In this way, a large portion of trench 124 is positioned adjacent to secondary fluid inlet region 126 shown in FIG. 6C. Secondary fluid inlet region 126 is at the intersection of second leg 110 and the remainder of catheter hub 106. Because trench 124 is positioned along fluid inlet region 126, a secondary fluid supply such as a dextrose solution can be provided under positive pressure via second leg 110 and pass into secondary lumen 116.

Figure 7A:
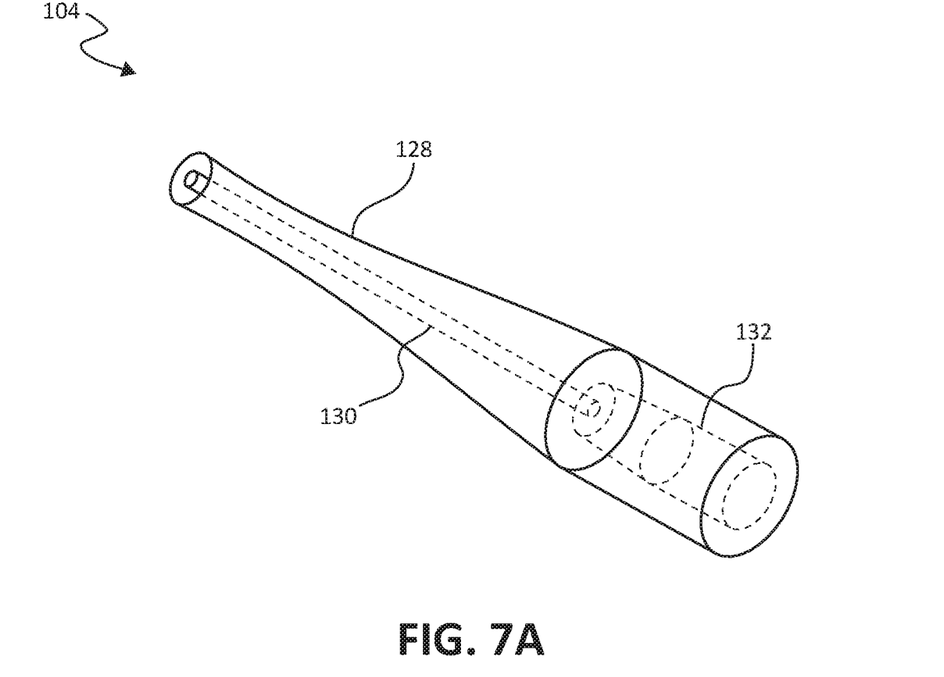
FIGS. 7A-7D depict the flexible plastic cover of FIGS. 1A-1B.
Figure 7B:
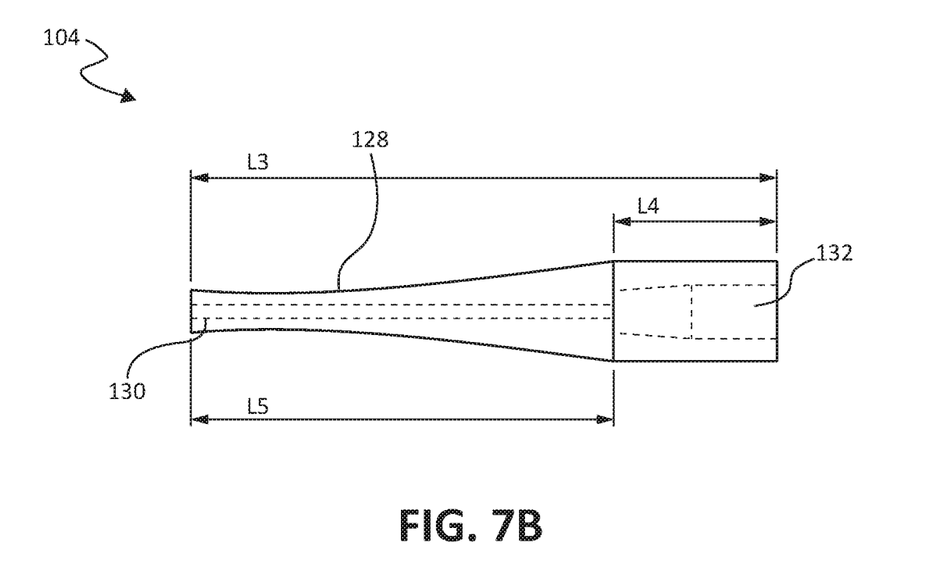

FIGS. 7A and 7B depict flexible cover 104. Flexible cover 104 includes a pliable portion 128 surrounding and defining a catheter pathway 130. Flexible cover 104 also includes an engagement portion 132 configured to attach to third leg 112 of catheter hub 106, as shown with respect to FIGS. 1A-1B. Flexible cover 104 can be made of a flexible plastic, for example, or some other elastomer that will permit catheter 102 to slide, but prevent fluid from passing between catheter 102 and flexible cover 104 within the pliable portion 128 range.

As shown in FIG. 7B, the total length L3 of flexible portion is about 1.380 inches. Of that length, engagement portion 132 accounts for a portion, L4, of about 0.380 inches, whereas pliable portion 128 accounts for a portion, L5, of about 1.000 inches. The relative lengths of the pliable portion 128 and engagement portion 132 can differ in various embodiments.

Figure 7C:
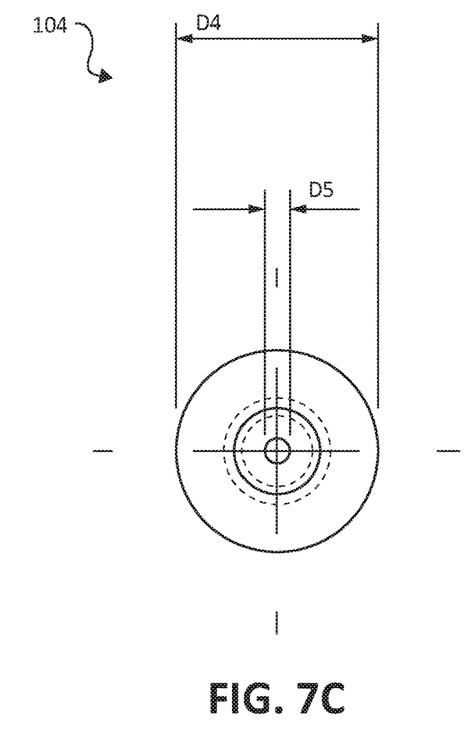
Figure 7D:
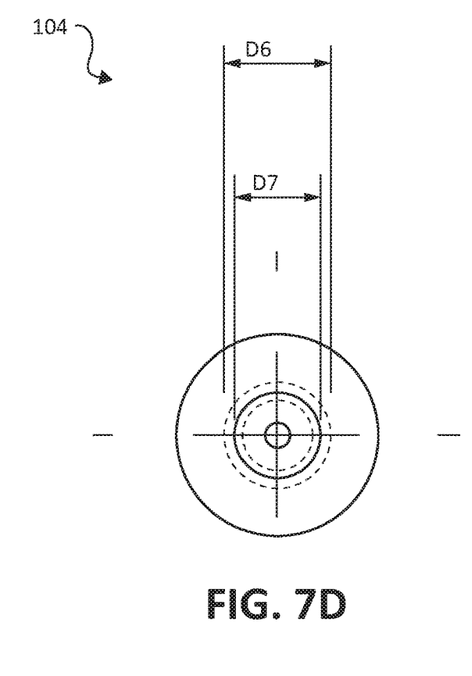

The inner and outer diameters of flexible cover 104 are depicted in FIGS. 7C and 7D. In particular, FIG. 7C shows flexible cover 104 from the proximal end, whereas FIG. 7D shows flexible cover 104 from the distal end. FIG. 7C illustrates fourth diameter D4 (the full radial extent of flexible cover 104), which is about 0.240 inches. FIG. 7C further illustrates fifth diameter D5 (the radius of the catheter pathway 130), which is about 0.030 inches. FIG. 7D illustrates sixth diameter D6 (the outer radius of pliable portion 128 at its furthest proximal extent), which is about 0.130 inches, and seventh diameter D7 (the outer radius of pliable portion 128 at its furthest distal extent), which is about 0.100 inches. Each of these dimensions can vary based upon the dimensions of the catheter, the materials used, or a number of other factors, and are meant to be merely illustrative of one embodiment.

In operation, starting from the configuration shown in FIG. 1B, the inner lumen of catheter 102 can be filled by a syringe or other fluid source attached to the first leg 108 of catheter hub 106. Second leg 110 can be used to provide the second fluid source that travels within the secondary lumen, as described in more detail with respect to FIGS. 6A-6C. In an embodiment, the second fluid source can be provided to catheter 102 via second leg 110, causing catheter 102 to discharge the second fluid around its radially exterior wall (118, FIGS. 2A and 2B) at and around its distal end. The resulting fluid coating on the radially exterior wall (118, FIGS. 2A and 2B) inhibits premature polymerization and therefore prevents sticking between catheter 102 and the embolization site.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A system for providing a first fluid and a second fluid, the system comprising:
    a catheter hub;
    a flexible cover configured to attach to the catheter hub and provide a seal with the catheter hub; and
    a catheter configured to be at least partially arranged within the catheter hub and the flexible cover and passing through the seal, the catheter defining:
        an outer circumference centered around a central axis;
        a primary lumen defined by a substantially solid wall having an inner diameter and an outer diameter that are each centered along the central axis, the primary lumen arranged within the inner diameter and including a primary lumen end aperture arranged at a distal end of the catheter, wherein the primary lumen is configured to provide the first fluid at the distal end of the catheter; and
        a secondary lumen defined within the substantially solid wall in a helical orbiting path around the primary lumen, the secondary lumen defining:
            a secondary lumen end aperture arranged adjacent to the primary lumen end aperture at the distal end of the catheter, the secondary lumen end aperture configured to comingle the second fluid and the first fluid proximate a distal tip of the catheter; and
            a plurality of side apertures arranged within and along the outer circumference, the plurality of side apertures configured to bathe the outer circumference in the second fluid such that premature polymerization and sticking of the catheter to an embolization site is inhibited.

2. The system of claim 1, wherein the catheter hub is a hemostatic valve.

3. The system of claim 1, wherein the catheter further comprises an inlet trench passing through the substantially solid wall at a proximal end thereof, wherein the inlet trench is in fluid communication with the secondary lumen.

4. The system of claim 3, wherein:
the catheter hub has first, second, and third legs;
the catheter is arranged at least partially within the third leg; and
the second leg and the inlet trench coincide at a fluid inlet region.

5. The system of claim 1, wherein:
the first fluid is an embolizing agent; and
the second fluid is a dextrose solution.

6. The system of claim 1, wherein when the catheter is arranged along a straight line from a distal end to a proximal end, the outer circumference of the catheter, the inner diameter of the substantially solid wall, and the outer diameter of the substantially solid wall are centered along the central axis, and the central axis is coaxial with the straight line.

7. A method comprising providing a catheter system for delivering a first fluid and a second fluid, the catheter system comprising:
a catheter hub;
a flexible cover configured to attach to the catheter hub and provide a seal with the catheter hub; and
a catheter configured to be at least partially arranged within the catheter hub and the flexible cover and passing through the seal, the catheter defining:
an outer circumference centered around a central axis;
a primary lumen defined by a substantially solid wall having an inner diameter and an outer diameter that are each centered along the central axis, the primary lumen arranged within the inner diameter and including a primary lumen end aperture arranged at a distal end of the catheter, wherein the primary lumen is configured to provide the first fluid at the distal end of the catheter; and
a secondary lumen arranged within the substantially solid wall in a helical orbiting path around the primary lumen, the secondary lumen including:
a secondary lumen end aperture arranged adjacent to the primary lumen end aperture at the distal end of the catheter, the secondary lumen end aperture configured to comingle the second fluid and the first fluid proximate a distal tip of the catheter; and
a plurality of side apertures arranged within and along the outer circumference, the plurality of side apertures configured to bathe the outer circumference in the second fluid such that premature polymerization and sticking of the catheter to an embolization site is inhibited.

8. The method of claim 7, wherein the providing further comprises forming the catheter system.

9. The method of claim 7, further comprising controlling the catheter system to deliver the first fluid and the second fluid.

10. A system for providing a first fluid and a second fluid, the system comprising:
a catheter hub;
a flexible cover configured to attach to the catheter hub and provide a seal with the catheter hub; and
a catheter configured to be at least partially arranged within the catheter hub and the flexible cover and passing through the seal, the catheter defining:
an outer circumference centered around a central axis;
a primary lumen defined by a substantially solid wall having an inner diameter and an outer diameter that are each centered along the central axis, the primary lumen arranged within the inner diameter and including a primary lumen end aperture arranged at a distal end of the catheter, wherein the primary lumen is configured to provide the first fluid at the distal end of the catheter; and
a secondary lumen arranged in the substantially solid wall between the inner diameter and the outer diameter, the secondary lumen including:
a secondary lumen end aperture arranged adjacent to the primary lumen end aperture at the distal end of the catheter, the secondary lumen end aperture configured to comingle the second fluid and the first fluid proximate a distal tip of the catheter; and
a plurality of side apertures arranged within and along the outer circumference, the plurality of side apertures configured to bathe the outer circumference in the second fluid such that premature polymerization and sticking of the catheter to an embolization site is inhibited.

* * * * *